United States Patent
Cheng et al.

(10) Patent No.: US 11,499,172 B2
(45) Date of Patent: Nov. 15, 2022

(54) USE OF STEREOSELECTIVE TRANSAMINASE IN ASYMMETRIC SYNTHESIS OF CHIRAL AMINE

(71) Applicant: ABIOCHEM BIOTECHNOLOGY CO., LTD, Shanghai (CN)

(72) Inventors: Zhanbing Cheng, Shanghai (CN); Tao Zhang, Shanghai (CN); Zhenhua Tian, Shanghai (CN); Shaonan Ding, Shanghai (CN)

(73) Assignee: Abiochem Biotechnology Co., Ltd., Shanghai (CN)

( * ) Notice: Subject to any disclaimer, the term of this patent is extended or adjusted under 35 U.S.C. 154(b) by 0 days.

(21) Appl. No.: 16/630,297

(22) PCT Filed: Jul. 10, 2018

(86) PCT No.: PCT/CN2018/095148
§ 371 (c)(1),
(2) Date: Jan. 10, 2020

(87) PCT Pub. No.: WO2019/011236
PCT Pub. Date: Jan. 17, 2019

(65) Prior Publication Data
US 2020/0157587 A1    May 21, 2020

(30) Foreign Application Priority Data
Jul. 11, 2017    (CN) .......................... 201710561640.3

(51) Int. Cl.
*C12P 13/06* (2006.01)
*C12N 9/10* (2006.01)
*C12P 13/00* (2006.01)

(52) U.S. Cl.
CPC ............ *C12P 13/06* (2013.01); *C12N 9/1096* (2013.01); *C12P 13/001* (2013.01)

(58) Field of Classification Search
None
See application file for complete search history.

(56) References Cited

U.S. PATENT DOCUMENTS

| 6,413,752 | B1 | 7/2002 | Takashima et al. |
| 8,293,507 | B2* | 10/2012 | Savile ............ C12Y 206/01018 |
| | | | 435/119 |
| 2012/0156706 | A1* | 6/2012 | Hoehne ................ C12N 9/1096 |
| | | | 435/16 |

FOREIGN PATENT DOCUMENTS

| CN | 103014081 A | | 4/2013 |
| CN | 104480155 A | | 4/2015 |
| CN | 104805069 A | * | 7/2015 |
| CN | 105018440 A | * | 11/2015 |
| CN | 105018440 A | | 11/2015 |
| WO | 2010099501 A2 | | 9/2010 |
| WO | WO-2019007146 A1 | * | 1/2019 ........... C12N 9/1096 |

OTHER PUBLICATIONS

Umbarger, Amino acid biosynthesis and its regulation, Ann. Rev. Biochem. 47, 1978, 533-606. (Year: 1978).*
Genbank, Accession No. CP006936.2, 2014, www.ncbi.nlm.gov. (Year: 2014).*
Xiong et al., Improving the production of 22-hydroxy-23,24-bisnorchol-4-ene-3-one from sterols in *Mycobacterium neoaurum* by increasing cell permeability and modifying multiple genes, Microb. Cell Fact. 16, 2017, 89. (Year: 2017).*
NCBI Reference Sequence: WP_030134134.1, Jul. 9, 2014.
Iwasaki, A. et al. "Microbial Synthesis of Chiral Amines by (R)-Specfic Transamination with *Arthrobacter* Sp. KNK168" Appl. Microbiol. Biotechnol. vol. 69, No. 5, Jul. 8, 2005. pp. 499-505.
Jia, Hongua et al. "Progress in Transaminase in Chiral Amine Synthesis" Modern Chemical Industry. vol. 32, No. 3. Mar. 31, 2012, pp. 16-20 and 22.

* cited by examiner

*Primary Examiner* — Robert B Mondesi
*Assistant Examiner* — Todd M Epstein
(74) *Attorney, Agent, or Firm* — Polsinelli PC

(57) ABSTRACT

Use of a stereoselective transaminase in the asymmetric synthesis of a chiral amine. In particular, provided is use of a polypeptide in the production of a chiral amine or a downstream product using a chiral amine as a precursor. Further provided is a method for producing a chiral amine, comprising culturing a strain expressing the polypeptide so as to obtain a chiral amine. Further provided are a chiral amine production strain and a method for constructing the chiral amine production strain. The stereoselective transaminase has a broad substrate spectrum and thus has a broad application potential in the preparation of a chiral amine.

8 Claims, No Drawings
Specification includes a Sequence Listing.

SEQUENCE LISTING

<160> NUMBER OF SEQ ID NOS: 4

<210> SEQ ID NO 1
<211> LENGTH: 335
<212> TYPE: PRT
<213> ORGANISM: Mycobacterium sp.

<400> SEQUENCE: 1

| | | | | | | | | | | | | | | | |
|---|---|---|---|---|---|---|---|---|---|---|---|---|---|---|---|
|Met|Ser|Thr|Gly|Thr|Ser|Asn|Leu|Val|Ala|Val|Glu|Pro|Gly|Ala|Ile|
|1| | | |5| | | | |10| | | | |15| |

Arg Glu Asp Thr Pro Pro Gly Ser Val Ile Gln Tyr Ser Asp Tyr Glu
                20                  25                  30

Leu Asp His Ser Ser Pro Phe Ala Gly Gly Val Ala Trp Ile Glu Gly
            35                  40                  45

Glu Phe Leu Pro Ala Glu Asp Ala Lys Ile Ser Ile Phe Asp Thr Gly
    50                  55                  60

Phe Gly His Ser Asp Leu Thr Tyr Thr Val Ala His Val Trp His Gly
65                  70                  75                  80

Asn Ile Phe Arg Leu Gly Asp His Leu Asp Arg Leu Leu Asp Gly Ala
                85                  90                  95

Arg Lys Leu Arg Leu Asp Ala Gly Tyr Thr Lys Asp Glu Leu Ala Asp
                100                 105                 110

Ile Thr Lys Gln Cys Val Ala Met Ser Gln Leu Arg Glu Ser Phe Val
            115                 120                 125

Asn Leu Thr Val Thr Arg Gly Tyr Gly Lys Arg Arg Gly Glu Lys Asp
130                 135                 140

Leu Ser Lys Leu Thr His Gln Val Tyr Ile Tyr Ala Ile Pro Tyr Leu
145                 150                 155                 160

Trp Ala Phe Pro Pro Ala Glu Gln Ile Phe Gly Thr Thr Ala Ile Val
                165                 170                 175

Pro Arg His Val Arg Arg Ala Gly Arg Asn Thr Val Asp Pro Thr Ile
                180                 185                 190

Lys Asn Tyr Gln Trp Gly Asp Leu Thr Ala Ala Ser Phe Glu Ala Lys
            195                 200                 205

Asp Arg Gly Ala Arg Thr Ala Ile Leu Leu Asp Ser Asp Asn Cys Val
210                 215                 220

Ala Glu Gly Pro Gly Phe Asn Val Cys Ile Val Lys Asp Gly Lys Leu
225                 230                 235                 240

Ala Ser Pro Ser Arg Asn Ala Leu Pro Gly Ile Thr Arg Lys Thr Val
                245                 250                 255

Phe Glu Leu Ala Glu Gln Met Gly Ile Glu Ala Thr Leu Arg Asp Val
            260                 265                 270

Thr Ser His Glu Leu Tyr Glu Ala Asp Glu Leu Met Ala Val Thr Thr
        275                 280                 285

Ala Gly Gly Val Thr Pro Ile Asn Ser Leu Asp Gly Glu Pro Ile Gly
290                 295                 300

Asn Gly Glu Pro Gly Glu Met Thr Val Ala Ile Arg Asp Arg Phe Trp
305                 310                 315                 320

Ala Leu Met Asp Glu Pro Gly Pro Leu Ile Glu Ala Ile Glu Tyr
                325                 330                 335

<210> SEQ ID NO 2
<211> LENGTH: 1008
<212> TYPE: DNA
<213> ORGANISM: Mycobacterium sp.

<400> SEQUENCE: 2
atgagcacag gaacctccaa cctcgtggcc gtcgaaccgg agccatccg ggaggacacc      60 ccgccggggt cggtgatcca gtacagcgat tacgagctgg accacagcag cccgttcgcc     120
ggcggcgtcg cctggatcga aggagagttc ctgcccgcgg aggatgccaa gatctccatc     180

```
ttcgacaccg gcttcgggca ttccgatctc acctacaccg tcgcgcatgt gtggcacggc    240
aacatcttcc ggctggggga tcacctggac cgactgctcg acggggcccg caagctgcgt    300
ctggacgccg gttacaccaa ggacgagttg gccgatatca ccaaacagtg cgtcgcgatg    360
tcgcagctgc gcgaatcctt cgtcaacctc accgttaccc ggggctacgg aaagcgaagg    420
ggcgaaaagg atctgtccaa gctgacccac caggtgtaca tctacgccat cccgtatctg    480
tgggcgttcc ccccggccga gcagatcttc ggcaccaccg ccatcgtgcc gcgccatgtc    540
cgtcgggccg ccgcaacac ggtggacccg accatcaaga actatcagtg gggcgatctg    600
accgcggcca gcttcgaggc caaggaccgc ggggcccgca ctgccatcct gctcgactcg    660
gacaactgtg tggccgaggg gccgggtttc aacgtctgca tcgtcaagga tggcaagctg    720
gcctccccgt cgcgaaatgc gttgccgggc atcacccgca agactgtttt cgaactcgcc    780
gagcagatgg gcatcgaggc caccctgcgc gatgtcacca gccacgaact ctacgaggcc    840
gacgagctga tggccgtcac caccgccggc ggtgtcaccc cgatcaactc cctggacggc    900
gagccgatcg gcaacggtga gcccggtgag atgacggtcg ccatccggga ccgcttctgg    960
gcgctgatgg acgagcccgg cccgctgatc gaagcgatcg aatactga              1008

<210> SEQ ID NO 3
<211> LENGTH: 41
<212> TYPE: DNA
<213> ORGANISM: Artificial sequence
<220> FEATURE:
<223> OTHER INFORMATION: Primer

<400> SEQUENCE: 3
ttaagaagga gatatacata tgagcacagg aacctccaac c                          41

<210> SEQ ID NO 4
<211> LENGTH: 41
<212> TYPE: DNA
<213> ORGANISM: Artificial sequence
<220> FEATURE:
<223> OTHER INFORMATION: Primer

<400> SEQUENCE: 4
ctcgagtgcg gccgcaagct tagtattcga tcgcttcgat c                          41
```

USE OF STEREOSELECTIVE TRANSAMINASE IN ASYMMETRIC SYNTHESIS OF CHIRAL AMINE

CROSS REFERENCE TO RELATED APPLICATIONS

The present application is U.S. National Stage Application under 35 U.S.C. § 371 of International Application No. PCT/CN2018/095148, filed on Jul. 7, 2018, which claims the benefit of Chinese Patent Application No. 20170561640.3, filed on Jul. 11, 2017, the contents of each of which are incorporated by reference herein in their entireties.

SEQUENCE LISTING

A Sequence Listing submitted on Jan. 10, 2021 as an ASCII text file via EFS-Web is hereby incorporated by reference in accordance with 35 U.S.C. § 1.52(e). The name of the ASCII text file for the Sequence Listing is SEQ.TXT, and the size of the ASCII text file is 29 KB.

TECHNICAL FIELD

The invention relates to the field of biotechnology, and particularly relates to a highly active transaminase, a use of the transaminase as a catalyst in asymmetric synthesis of chiral amines, and a method for producing chiral amines.

BACKGROUND

Chiral amines are important intermediates and active ingredients in many drugs. For example, (3R)-3-amino-1-[3-(trifluoromethyl)-5,6-dihydro-1,2,4-triazolo[4,3-a] pyrazine-7 (8H)-yl]-4-(2,4,5-trifluorophenyl) butan-1-one is an effective ingredient for treating type II diabetes. However, it is difficult to obtain optically pure products by existing organic synthesis methods, which usually require metal catalysts for asymmetric synthesis and are expensive, with metal residue and difficult post processing. Therefore, there is an urgent need to develop environmental methods for the production of chiral amines.

Transaminase, also known as aminotransferase, is a type of enzyme that catalyzes the reversible transfer of amino groups between amino compounds and carbonyl compounds. According to the position of amino group as the aminotransferases' substrate, they can be divided into a-transaminase and ω-transaminase. a-transaminase is more common and can only catalyze the transfer of a-amino groups. ω-transaminase is relatively rare. In addition to catalyzing the transfer of a-amino groups, ω-transaminase can also catalyze the transfer of non-a-amino groups. It has wider substrate spectrum and stricter stereoselectivity, which can catalyze prochiral carbonyl compounds to produce chiral amines under mild reaction conditions. In addition, ω-transaminase takes pyridoxal phosphate as a prosthetic group and no additional co-factor cycle is needed in the catalytic reaction process, which is advantageous for industrial production.

For example, the US patent U.S. Pat. No. 8,293,507 discloses that the biocatalyst obtained by Codexis by engineering ω-transaminase derived from *Arthrobacter* replaces the rhodium catalyst in the chemical process, and the transamination product has an ee value of 99% with a substrate feed of 100 g/L.

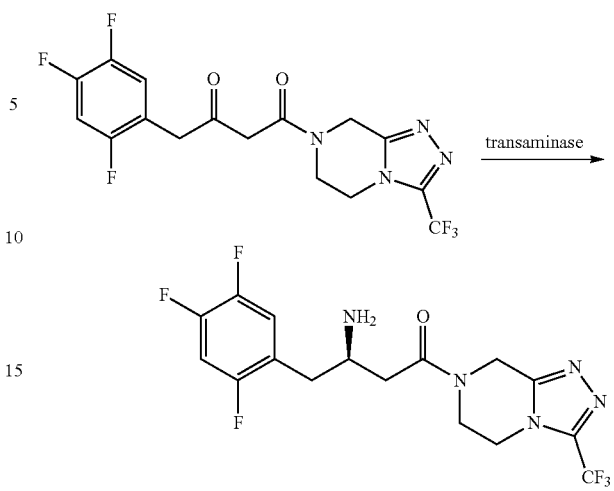

Due to the stereoisomerism specificity of the enzyme, it is very important to obtain a specific stereoselective enzyme. It has been reported in the literature that among ω-transaminases, S-selective enzymes are more common, while R-selective enzymes are relatively rare. Therefore, it is of great significance to discover an R-selective ω-transaminase with industrial application prospects for the production of chiral amines.

SUMMARY OF THE INVENTION

One of the objects of the present invention is to provide an use of a polypeptide in the production of a chiral amine or a downstream product with the chiral amine as precursor.

Another object of the present invention is to provide a method for producing chiral amines.

Another object of the present invention is to provide a chiral amine producing strain.

Another object of the present invention is to provide a method for constructing a chiral amine producing strain.

In a first aspect of the invention, it provides a use of a polypeptide in the production of a chiral amine or a downstream product with the chiral amine as precursor, wherein the polypeptide is:
  (a1) a polypeptide having an amino acid sequence shown in SEQ ID NO: 1; or
  (b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (a1).

In another preferred embodiment, the chiral amine is formed by an asymmetric synthesis reaction of a prochiral carbonyl compound.

In another preferred embodiment, the prochiral carbonyl compound is selected from the group consisting of:

1

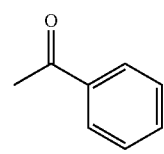

-continued

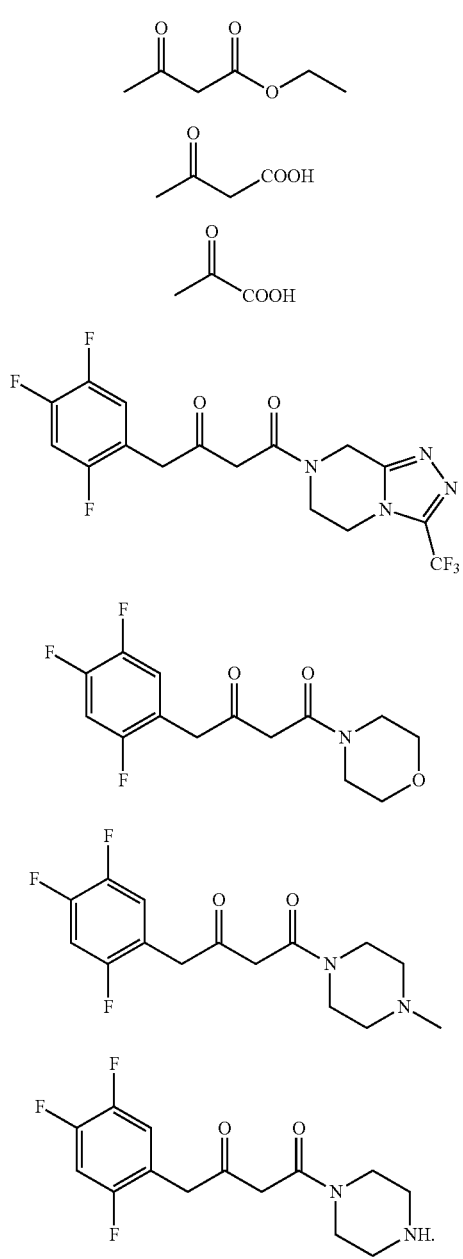

In another preferred embodiment, the polypeptide of (b1) is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

In another preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In another preferred embodiment, the chiral amine includes the following compounds 1a-8a or a pharmaceutically acceptable salt thereof:

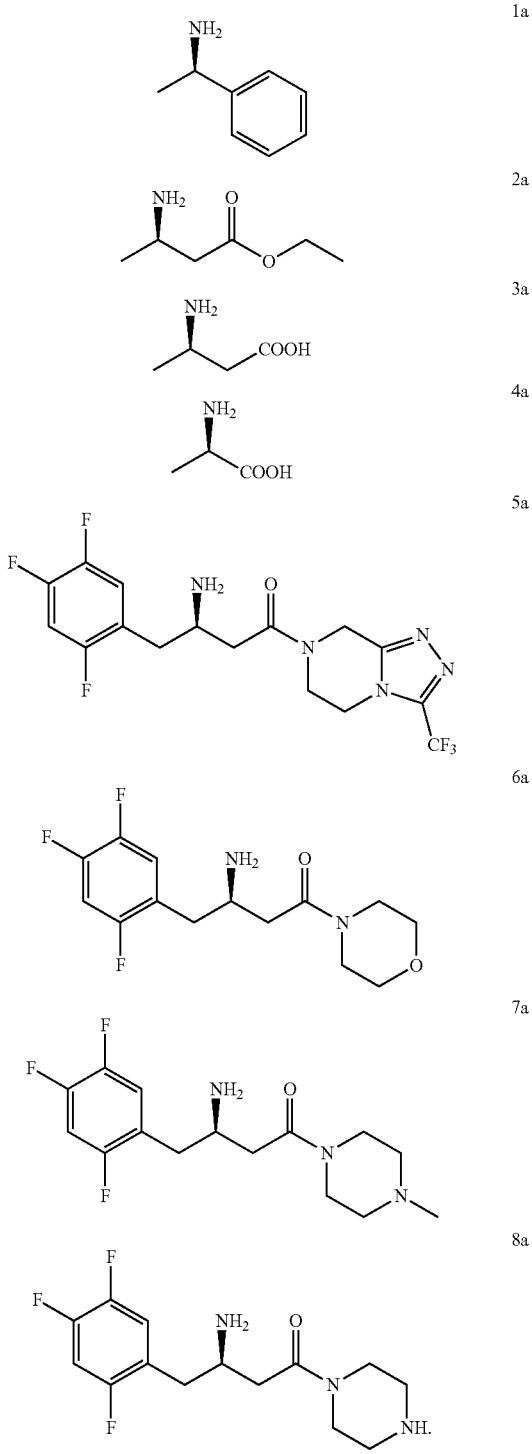

In another preferred embodiment, the downstream product with the chiral amine as precursor includes: sitagliptin (compound 5a), raw material of a chiral acid resolving agent or a chiral drug intermediate (compound 1a), dolutegravir intermediate (compound 3a), and raw material of a chiral drug intermediate (compound 2a, compound 4a), sitagliptin intermediate (compound 6a, compound 7a, and compound 8a).

In a second aspect of the invention, it provides a method for producing a chiral amine, which comprises:
(a) carrying out a reaction shown in equation I to form a chiral amine in a liquid reaction system, using a prochiral carbonyl compound as a substrate, in the presence of a prosthetic group and under the catalysis of stereoselective transaminase;

$$\text{prochiral carbonyl compound} + \text{amino donor} \xrightarrow{\text{stereoselective transaminase}}$$
$$\text{chiral amine} + \text{carbonyl compound after deamination of amino donor}$$
(I)

(b) optionally isolating the chiral amine from the reaction system after the reaction of the previous step.

In another preferred embodiment, the concentration of the prochiral carbonyl compound in the reaction system is 1 g/L-1000 g/L, preferably 5 g/L-500 g/L, more preferably 10 g/L-100 g/L, more preferably 5 g/L-50 g/L, and most preferably 20 g/L-50 g/L.

In another preferred embodiment, the concentration of the stereoselective transaminase protein in the reaction system is 1-500 mg/mL, preferably 5-200 mg/mL, more preferably 10-100 mg/mL, and most preferably 20-80 mg/mL.

In another preferred embodiment, the stereoselective transaminase is:
(a1) a polypeptide having an amino acid sequence shown in SEQ ID NO: 1; or
(b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (a1).

In another preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In another preferred embodiment, the prochiral carbonyl compound is selected from the group consisting of:

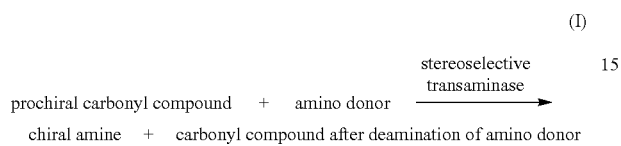

1

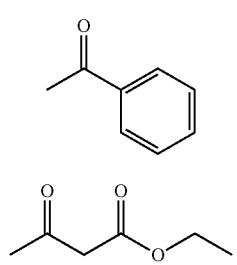

2

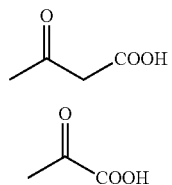

3

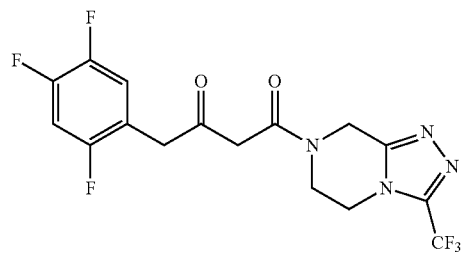

4

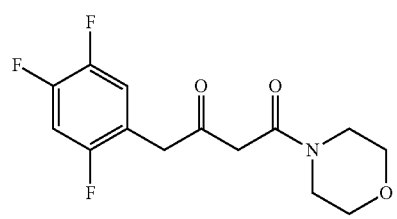 [SMILES: O=C(CC(=O)N1CCOCC1)Cc1cc(F)c(F)cc1F]

5

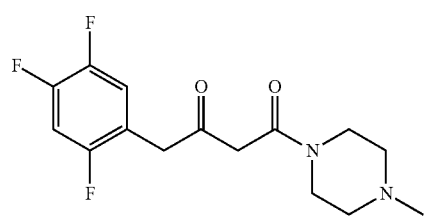

6

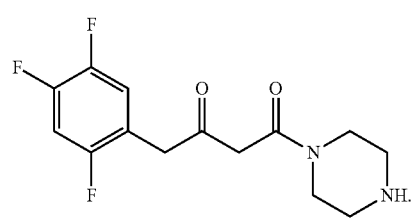

7

8

In another preferred embodiment, the prosthetic group is pyridoxal phosphate.

In another preferred embodiment, the concentration of the prosthetic group in the reaction system is 1-200 mM, preferably 5-150 mM, more preferably 10-100 mM, and most preferably 5-50 mM.

In another preferred embodiment, the temperature in step (a) is 5-50° C., preferably 10-45° C., more preferably 20-40° C., and most preferably 25-35° C.

In another preferred embodiment, the pH in step (a) is 6-10, preferably 7-10, more preferably 7.5-8.5.

In a third aspect of the invention, it provides a chiral amine producing strain expressing the following polypeptide:
(a1) a polypeptide having an amino acid sequence shown in SEQ ID NO: 1; or
(b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (A).

In another preferred embodiment, the polypeptide is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

In another preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In another preferred embodiment, the producing strain is a bacteria.

In another preferred embodiment, the bacteria is *Escherichia coli*.

In another preferred embodiment, the *Escherichia coli* is *Escherichia coli* BL21.

In a fourth aspect of the invention, it provides a method for producing a chiral amine, which comprises the steps of:
1) culturing the producing strain of the third aspect of the invention under production conditions to obtain a chiral amine;
2) optionally isolating the chiral amine from the culture system of 1).

In another preferred embodiment, an appropriate amount of pyridoxal phosphate is added in step 1) of the method.

In a fifth aspect of the invention, it provides a method for constructing a chiral amine producing strain, which comprises:
modifying the strain to comprise an expression vector expressing the following polypeptide or to integrate a gene expressing the following polypeptide into its genome, and the polypeptide is:
(a1) a polypeptide having an amino acid sequence shown in SEQ ID NO: 1; or
(b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (a1).

In another preferred embodiment, the polypeptide of (b1) is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

In another preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In another preferred embodiment, the sequence of the gene is selected from the group consisting of:
(i) the sequence shown in SEQ ID NO: 2;
(ii) a polynucleotide sequence complementary to the sequence defined in (i); or
(iii) any polynucleotide sequence having at least 70% (preferably at least 75%, 80%, 85%, 90%, more preferably at least 95%, 96%, 97%, 98%, 99%) sequence identity of the sequence defined in (i), or a complementary sequence thereof.

In another preferred embodiment, the gene is constructed on an expression vector.

In a sixth aspect of the invention, it provides a compound of formula II, or a pharmaceutically acceptable salt thereof, or a stereoisomer thereof:

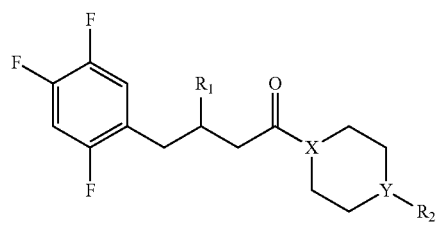

II wherein, $R_1$ is selected from the group consisting of: none, oxo (=O), halogen, —OH, —NH$_2$, substituted or unsubstituted $C_1$-$C_5$ alkyl, substituted or unsubstituted $C_3$-$C_8$ cycloalkyl, substituted or unsubstituted $C_1$-$C_8$ alkoxy, substituted and unsubstituted $C_3$-$C_8$ cycloalkoxy;

$R_2$ is selected from the group consisting of: none, halogen, —OH, —NH$_2$, substituted or unsubstituted $C_1$-$C_5$ alkyl, substituted or unsubstituted $C_3$-$C_8$ cycloalkyl, substituted or unsubstituted $C_1$-$C_8$ alkoxy, substituted and unsubstituted $C_3$-$C_8$ cycloalkoxy;

X is selected from the group consisting of: C and N;

Y is selected from the group consisting of: C, N, O, and S;

Wherein $R_2$ is none when Y is O or S.

In another preferred embodiment, $R_1$ is oxo (=O).

In another preferred embodiment, $R_1$ is —NH$_2$.

In another preferred embodiment, X is N.

In another preferred embodiment, Y is O.

In another preferred embodiment, the compound of formula II includes the following compounds:

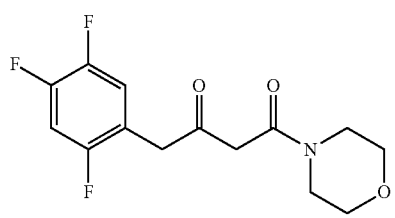

6

-continued

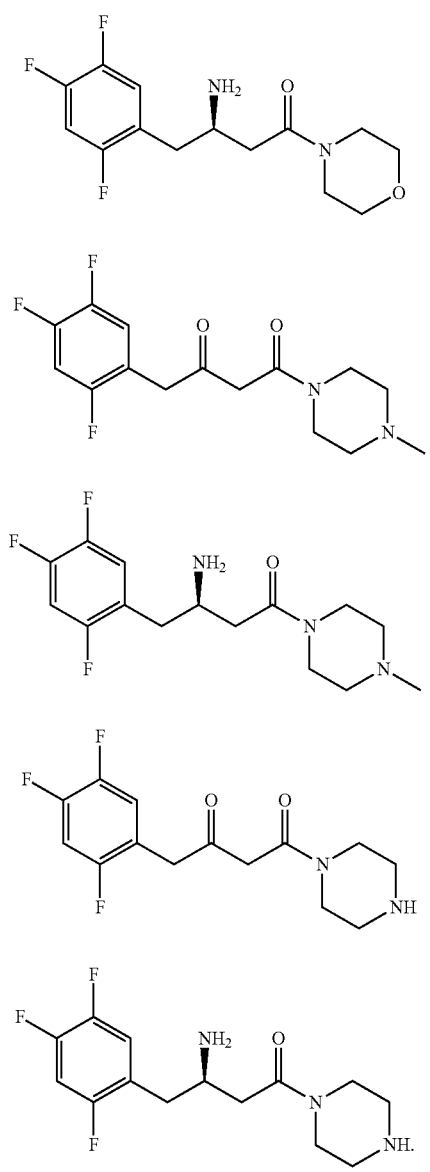

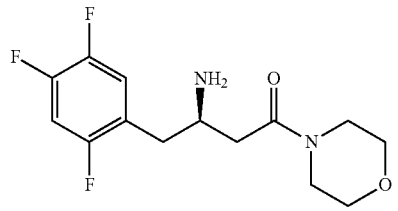

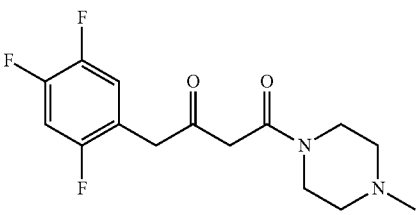 [SMILES: CN1CCN(C(=O)CC(=O)Cc2cc(F)c(F)cc2F)CC1]

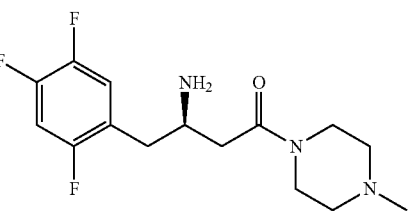

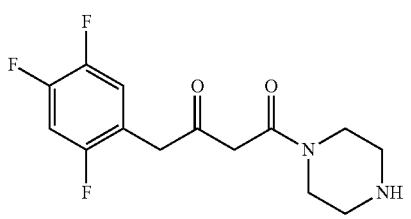 [SMILES: O=C(CC(=O)N1CCNCC1)Cc1cc(F)c(F)cc1F]

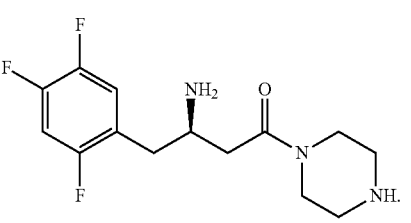

In a seventh aspect of the invention, it provides a use of the compound of the sixth aspect of the invention, or a pharmaceutically acceptable salt thereof, or a stereoisomer thereof, for preparing a sitagliptin intermediate Boc-(R)-3-amino-4-(2,4,5-trifluorophenyl) butyric acid.

In another preferred embodiment, the compound of formula II includes the following compounds:

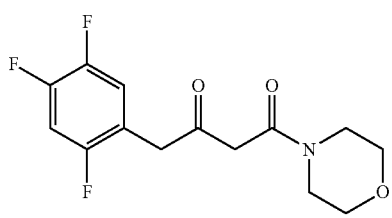

It is to be understood that the various technical features of the present invention mentioned above and the various technical features specifically described hereinafter (as in the Examples) may be combined with each other within the scope of the present invention to constitute a new or preferred technical solution, which will not be repeated one by one herein, due to space limitations.

DETAILED DESCRIPTION

After extensive and intensive studies, the inventors have unexpectedly discovered a polypeptide (ω-transaminase) which can be used as a stereoselective catalyst to efficiently convert a prochiral carbonyl compound to an R stereoselective chiral amine. The ω-transaminase according to the present invention has strict R stereoselectivity and a wide substrate spectrum, and has great application prospects in the production of chiral amines and chiral drugs. The present invention is completed on this basis.

Definitions

Unless otherwise defined, all technical and scientific terms used herein have the same meaning as commonly understood by one ordinary skill in the art of the invention.

As used herein, when used in reference to a particular recited value, the term "about" means that the value can vary by no more than 1% from the recited value. For example, as used herein, the expression "about 100" comprises all values between 99 and 101 (eg, 99.1, 99.2, 99.3, 99.4, etc.).

As used herein, the term "including" or "comprising (comprise)" may be open, semi-closed, and closed. In other words, the term also includes "essentially consisting of" or "consisting of".

Unless otherwise defined, the following terms used in the specification and claims have meanings as commonly understood by a person skilled in the art. Unless otherwise stated, all patents, patent applications, and published materials cited herein are incorporated by reference in their entirety.

It should be understood that the above brief description and the following detailed description are exemplary and explanatory only and are not restrictive of the subject matter of the invention. In the application, the singular used includes the plural unless otherwise specifically stated. It must be noted that the singular form used in the specification and claims includes the plural form of the referenced thing unless otherwise clearly stated in the context. It should also be noted that "or", "either" is used to mean "and/or" unless otherwise stated. In addition, the term "including" or "comprising (comprise)" may be open, semi-closed, and closed. In other words, the term also includes "essentially consisting of" or "consisting of".

Definitions of standard chemical terms can be found in references (including Carey and Sundberg "ADVANCED ORGANIC CHEMISTRY 4TH ED." Vols. A (2000) and B (2001), Plenum Press, New York). Unless otherwise stated, conventional methods within the skill of the art, such as mass spectrometry, NMR, IR, and UV/VIS spectroscopy and pharmacological methods, are used. Unless specifically defined, the terms used in the descriptions of analytical chemistry, organic synthetic chemistry, and medicinal and medicinal chemistry are known in the art. Standard techniques can be used in chemical synthesis, chemical analysis, drug preparation, formulation and delivery, and treatment of patients. For example, the reaction and purification can be performed according to a manufacturer's instruction for use of a kit, or according to a manner known in the art or the description of the invention. The techniques and methods described above can generally be implemented according to conventional methods well known in the art, based on descriptions in several summary and more specific literatures cited and discussed in the specification. In the specification, groups and their substituents may be selected by the skilled in the art to provide stable moieties and compounds.

When a substituent is described by a conventional chemical formula written from left to right, the substituent also includes a chemically equivalent substituent obtained when the structural formula is written from right to left. For example, —CH$_2$O— is equivalent to —OCH$_2$—.

The captions used herein are for organizational purposes only and should not be construed as restriction of the subject matter. All literatures or parts of literatures cited in the application, including but not limited to patents, patent applications, articles, books, operating manuals and papers, are incorporated herein by reference in their entirety.

In front of certain chemical groups defined herein, a simplified symbol is used to represent the total number of carbon atoms present in the group. For example, C1-C6 alkyl refers to an alkyl group as defined below having a total of 1 to 6 carbon atoms. The total number of carbon atoms in the simplified symbol does not include the number of carbons that may be present in the substituents of the group.

In addition to the foregoing, when used in the specification and claims of the present application, the following terms have the meanings indicated below, unless specifically stated otherwise.

In the present application, the term "halogen" refers to fluorine, chlorine, bromine or iodine.

"Hydroxy" refers to —OH group.

In the present application, as a group or part of another group (for example, used in a group such as a halogen-substituted alkyl group), the term "alkyl" refers to a fully saturated straight or branched hydrocarbon chain group, and consists of only carbon and hydrogen atoms, which has, for example, 1 to 7 carbon atoms, and is connected to the rest of the molecule by a single bond. For example, the term "alkyl" includes but is not limited to methyl, ethyl, n-propyl, isopropyl, n-butyl, isobutyl, sec-butyl, tert-butyl, n-pentyl, 2-methylbutyl, 2, 2-dimethylpropyl, n-hexyl, heptyl and the like.

Polypeptide

As used herein, the term "polypeptide" or "polypeptide of the invention" or "polypeptide of the present invention" or "ω-transaminase" or "stereoselective transaminase" has same meaning, and is used interchangeably herein. All of them refer to a protein that catalyzes the production of chiral amines by a prechiral carbonyl compound. The polypeptide is not naturally existed in *E. coli*, which is an exogenous protein.

Based on the knowledge of the prior art, it is not difficult for the ordinary skilled in the art to know that the change of a few amino acid residues in certain regions of a polypeptide, such as non-important regions, will not substantially change the biological activity. For example, the sequence obtained by appropriate substitution of certain amino acids do not affect the activity (see Watson et al., Molecular Biology of The Gene, Fourth Edition, 1987, The Benjamin/Cummings Pub. Co. P224). Thus, an ordinary skilled in the art would be able to perform such a substitution and ensure that the obtained molecule still has the desired biological activity.

Therefore, in a specific embodiment, the polypeptide of the invention may be: (a1) a polypeptide having an amino acid sequence shown in SEQ ID NO: 1; or (b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (a1).

In a preferred embodiment, the polypeptide is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

In a preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In a specific embodiment, the polypeptide of the invention represents a protein having an amino acid sequence as shown in SEQ ID NO: 1, and the coding sequence thereof is shown as SEQ ID NO: 2.

In the present invention, the polypeptide of the invention includes a mutant in which at most 20, preferably at most 10, still preferably at most 3, more preferably at most 2, and most preferably at most 1 amino acid is substituted by an amino acid of similar or close property in comparison with the polypeptide having an amino acid sequence as shown in SEQ ID NO: 1. These mutants with conservative variant are formed by amino acid substitutions as shown in the table below.

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the polynucleotide encoding the polypeptide of the present invention. The term "polynucleotide encoding a polypeptide" may include a polynucleotide that encodes the polypeptide, or a polynucleotide that also comprises additional coding and/or non-coding sequences.

Therefore, as used herein, "comprising", "having" or "including" includes "containing", "consisting mainly of", "consisting essentially of", and "consisting of". "Consisting mainly of", "consisting essentially of" and "consisting of" are subordinate concepts of "comprising", "having" or "including".

In a specific embodiment, the homology or sequence identity may be 80% or more, preferably 90% or more, more preferably 95%-98%, and most preferably 99% or more.

Method for determining sequence homology or identity that are well known to the ordinary skilled in the art includes, but are not limited to: Computer Molecular Biology, edited by Lesk, A. M., Oxford University Press, New York, 1988; Biocomputing: Informatics and Genome Projects, edited by Smith, D. W., Academic Press, New York, 1993; Computer Analysis of Sequence Data, Part I, edited by Griffin, A. M, and Griffin, H. G., Humana Press, New Jersey, 1994; Sequence Analysis in Molecular Biology, von Heinje, G., Academic Press, 1987, and Sequence Analysis Primer, edited by Gribskov, M, and Devereux, J., M Stockton Press, New York, 1991 and Carillo, H. & Lipman, D., SIAM J. Applied Math., 48:1073(1988). The preferred method for determining identity is to obtain the greatest match between the sequences tested. Methods for determining identity are compiled into publicly available computer programs. Preferred computer program method for determining identity between two sequences includes, but are not limited to, the GCG software package (Devereux, J. et al., 1984), BLASTP, BLASTN, and FASTA (Altschul, S, F. et al., 1990). The BLASTX program is available to the public from NCBI and other sources (BLAST Handbook, Altschul, S. et al., NCBI NLM NIH Bethesda, Md. 20894; Altschul, S. et al., 1990). The well-known Smith Waterman algorithm can also be used to determine identity.

The Use of the Polypeptide

The inventors have unexpectedly discovered that the polypeptide of the present invention has a stereoselective transaminase (ω-transaminase) activity and can be used to produce a chiral amine or a downstream product with chiral amine as precursor.

In a specific embodiment, the polypeptide is:
(a1) a polypeptide having an amino acid sequence shown in SEQ ID NO: 1; or
(b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (a1).

In a preferred embodiment, the chiral amine is formed by an asymmetric synthesis reaction of a prochiral carbonyl compound.

In a preferred embodiment, the prochiral carbonyl compound is selected from the prochiral carbonyl compounds corresponding to the amino donors in Table 2 and the amino acceptor compounds in Table 3.

Typically, the prochiral carbonyl compound is selected from the group consisting of:

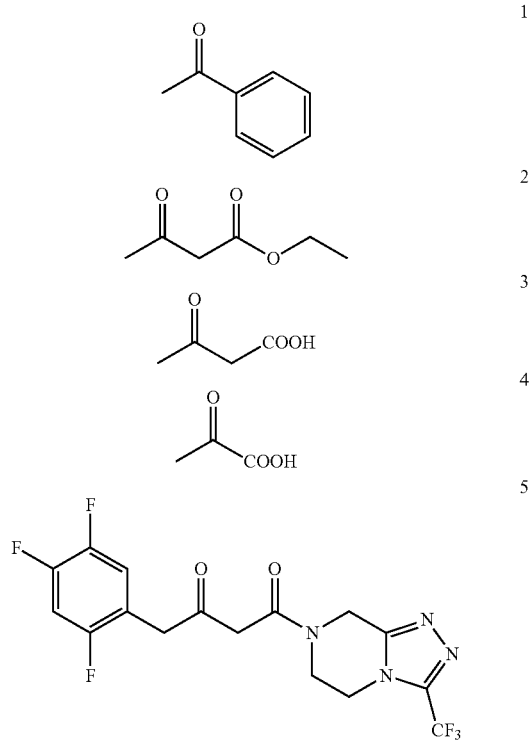

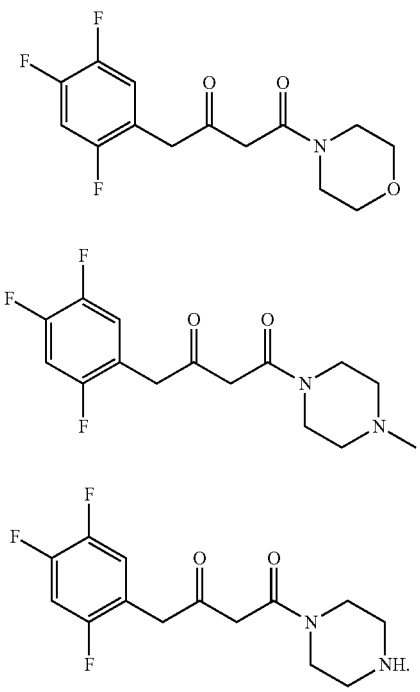

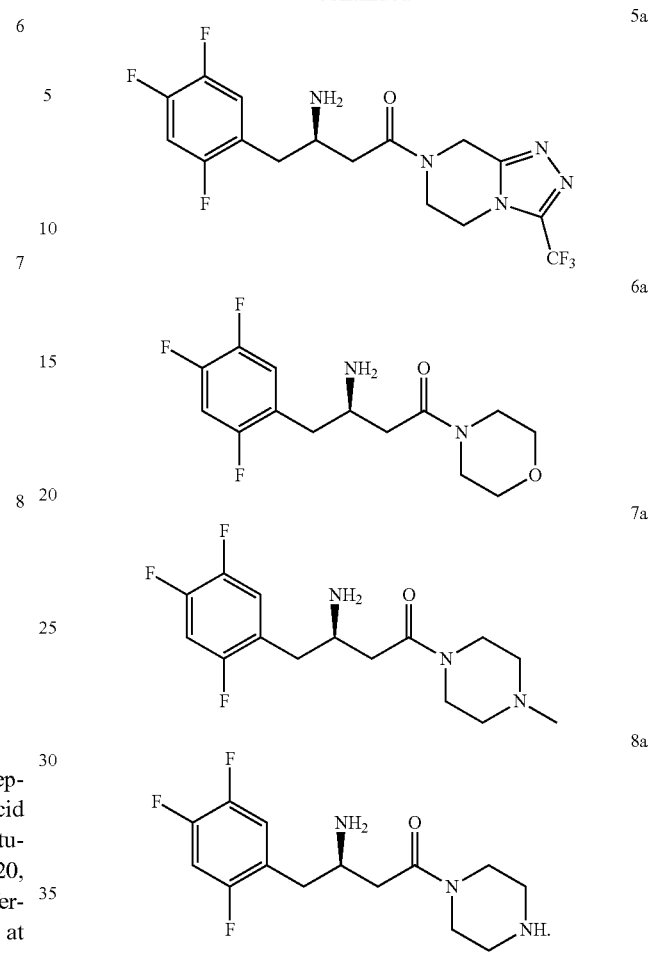

In a preferred embodiment, the polypeptide is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

Typically, the amino acid sequence of the polypeptide is shown in SEQ ID NO: 1.

In a preferred embodiment, the chiral amine includes compounds 1a-8a or a pharmaceutically acceptable salt thereof:

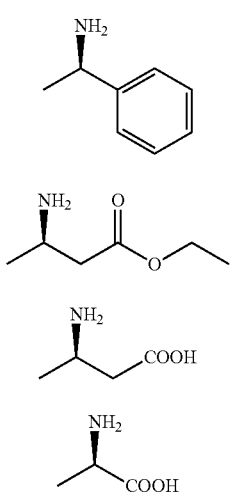

In a preferred embodiment, the downstream products with the chiral amine as precursor include: sitagliptin (compound 5a), raw material of a chiral acid resolving agent or a chiral drug intermediate (compound 1a), dolutegravir intermediate (compound 3a), raw material of a chiral drug intermediate (compound 2a, compound 4a), sitagliptin intermediate (compound 6a, compound 7a, compound 8a).

Chiral Amine Producing Strain

The inventors have unexpectedly discovered that a strain expressing the polypeptide of the invention can stereoselectively catalyzes the reaction shown in equation (I) to convert a prochiral carbonyl compound to a chiral amine (for example R-chiral amine).

In a specific embodiment, the strain expresses the following polypeptide:
- (a1) a polypeptide having an amino acid sequence shown in SEQ ID NO: 1; or
- (b1) a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) in the amino acid sequence shown in SEQ ID NO: 1, and having the function of the polypeptide of (A).

In another preferred embodiment, the polypeptide is a polypeptide derived from the polypeptide having an amino acid sequence shown in SEQ ID NO: 1 and formed by substitution, deletion, or addition of one or more, preferably 1-20, more preferably 1-15, more preferably 1-10, more preferably 1-3, and most preferably one amino acid residue(s) at either end of the amino acid sequence shown in SEQ ID NO: 1, and having the function of the polypeptide of (a1).

In another preferred embodiment, the amino acid sequence of the polypeptide is as shown in SEQ ID NO: 1.

In another preferred embodiment, the amino acid sequence of the polypeptide is any polypeptide sequence that has at least 70%, preferably at least 75%, 80%, 85%, 90%, and more preferably at least 95%, 96%, 97%, 98%, or 99% sequence identity of the amino acid sequence shown in SEQ ID NO: 1.

In another preferred embodiment, the producing strain is a bacteria, preferably *Escherichia coli* (eg, *E. coli* BL21).

Method for Producing Chiral Amines

In the present invention, the stereoselective transaminase (ω-transaminase) can be used in various forms. For example, resting cells or wet cells expressing the ω-transaminase of the invention can be used. Various forms such as crude enzyme solution, pure enzyme, crude enzyme powder or immobilized enzyme can also be used.

In a preferred embodiment, the method for producing chiral amines comprises:
(a) carrying out a reaction shown in equation I to form a chiral amine in a liquid reaction system, using prochiral carbonyl compound as a substrate, in the presence of a prosthetic group and under the catalysis of stereoselective transaminase;

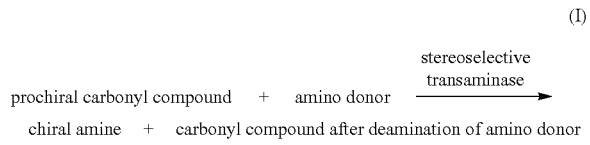

(I)

(b) optionally, isolating the chiral amine from the reaction system after the reaction of the previous step.

In another preferred embodiment, the method for producing a chiral amine includes:
1) culturing the chiral amine producing strain of the invention under production conditions to obtain a chiral amine;
2) optionally isolating the chiral amine from the culture system of 1).

In another preferred embodiment, an appropriate amount of pyridoxal phosphate is added in step 1) of the method for producing a chiral amine.

Construction Method of Chiral Amine Producing Strain

The inventors have unexpectedly discovered that a producing strain of chiral amine with high conversion rate can be constructed by modifying the strain to comprise an expression vector expressing the polypeptide of the invention or to integrate a gene expressing the polypeptide into its genome.

In another specific embodiment, the method further comprises measuring the conversion rate of the obtained strain and/or the chiral amine yield to verify the obtained strain.

The main advantages of the invention are:
(1) The new ω-transaminase disclosed in the invention has strict R stereoselectivity and a wide substrate spectrum, showing industrial application prospects in the environmental production of chiral amines and unnatural amino acids.

The present invention will be further illustrated below with reference to the specific examples. It is to be understood that these examples are for illustrative purposes only and are not intended to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers. Percentages and parts are by weight unless otherwise stated.

The reagents and raw materials used in the invention are all commercially available. Unless defined otherwise, all technical and scientific terms used herein have the same meanings as commonly understood by the ordinary skilled in the art to which the invention belongs. Although any methods and materials similar or equivalent to those described herein can be used in the practice or testing of the present invention, the methods and materials described herein are preferred.

Example 1 *Mycobacterium neoaurum* Transaminase

*Mycobacterium neoaurum* (*Mycobacterium* sp. NRRL B-3805) was purchased from the collection center, and the collection number is CP011022.1:988057-989064. Primers for PCR were designed based on the sequence of the transaminase of *Mycobacterium neoaurum* (see Table 1).

TABLE 1

| sequence list of primers | |
|---|---|
| MyTA-for | TTAAGAAGGAGAtatacatATGAGCACAGGAACCTCCAACC (SEQ ID No: 3) |
| MyTA-Rev | CTCGAGTGCGGCCGCaagcTTAGTATTCGATCGCTTCGATC (SEQ ID No: 4) |

*Mycobacterium* transaminase genomic DNA was used as a template for PCR amplification. The PCR amplification was performed with PCR system comprising 2 μL of 10×KOD-Plus PCR buffer, 1.2 μL of 25 mM MgSO₄, 2 μL of 2 mM dNTP, 0.3 μL of KOD-Plus PCR high fidelity enzyme, 0.5 μL of DNA template (including 0.1 μg of DNA template), 13 μL of ddH₂O, and 0.5 μL (10 mmol/L) of both forward and reverse primers of gene clone in Table 1. The PCR amplification steps were: (1) pre-denaturing at 95° C. for 3 min; (2) denaturing at 98° C. for 15 s; (3) annealing at 55° C. for 30 s; (4) extending at 72° C. for 1 min; wherein steps (2) to (4) repeated 30 times; (5) continuing the extending at 72° C. for 10 minutes and cooling to 4° C. The PCR product was purified by agarose gel electrophoresis. The agarose gel DNA recovery kit was used to recover the target band in the 900-1200 bp to obtain a complete full-length *Mycobacterium* transaminase gene sequence. After DNA sequencing, the full-length was identified with a length of 1008 bp and named MyTA. Its nucleotide sequence and encoded amino acid sequence are shown as SEQ ID No: 2 and 1 in the sequence listing, respectively.

SEQ ID No: 1
MSTGTSNLVAVEPGAIREDTPPGSVIQYSDYELDHSSPFAGGVAWIEGEF

LPAEDAKISIFDTGFGHSDLTYTVAHVWHGNIFRLGDHLDRLLDGARKLR

LDAGYTKDELADITKQCVAMSQLRESFVNLTVTRGYGKRRGEKDLSKLTH

-continued

QVYIYAIPYLWAFPPAEQIFGTTAIVPRHVRRAGRNTVDPTIKNYQWGDL

TAASFEAKDRGARTAILLDSDNCVAEGPGFNVCIVKDGKLASPSRNALPG

ITRKTVFELAEQMGIEATLRDVTSHELYEADELMAVTTAGGVTPINSLDG

EPIGNGEPGEMTVAIRDRFWALMDEPGPLIEAIEY

SEQ ID No: 2
ATGAGCACAGGAACCTCCAACCTCGTGGCCGTCGAACCGGGAGCCATCCG

GGAGGACACCCCGCCGGGGTCGGTGATCCAGTACAGCGATTACGAGCTGG

ACCACAGCAGCCCGTTCGCCGGCGGCGTCGCCTGGATCGAAGGAGAGTTC

CTGCCCGCGGAGGATGCCAAGATCTCCATCTTCGACACCGGCTTCGGGCA

TTCCGATCTCACCTACACCGTCGCGCATGTGTGGCACGGCAACATCTTCC

GGCTGGGGGATCACCTGGACCGACTGCTCGACGGGGCCCGCAAGCTGCGT

CTGGACGCCGGTTACACCAAGGACGAGTTGGCCGATATCACCAAACAGTG

CGTCGCGATGTCGCAGCTGCGCGAATCCTTCGTCAACCTCACCGTTACCC

GGGGCTACGGAAAGCGAAGGGGCGAAAAGGATCTGTCCAAGCTGACCCAC

CAGGTGTACATCTACGCCATCCCGTATCTGTGGGCGTTCCCCCCGGCCGA

GCAGATCTTCGGCACCACCGCCATCGTGCCGCGCCATGTCCGTCGGGCCG

GCCGCAACACGGTGGACCCGACCATCAAGAACTATCAGTGGGGCGATCTG

ACCGCGGCCAGCTTCGAGGCCAAGGACCGCGGGGCCCGCACTGCCATCCT

GCTCGACTCGGACAACTGTGTGGCCGAGGGGCCGGGTTTCAACGTCTGCA

TCGTCAAGGATGGCAAGCTGGCCTCCCCGTCGCGAAATGCGTTGCCGGGC

ATCACCCGCAAGACTGTTTTCGAACTCGCCGAGCAGATGGGCATCGAGGC

CACCCTGCGCGATGTCACCAGCCACGAACTCTACGAGGCCGACGAGCTGA

TGGCCGTCACCACCGCCGGCGGTGTCACCCCGATCAACTCCCTGGACGGC

GAGCCGATCGGCAACGGTGAGCCCGGTGAGATGACGGTCGCCATCCGGGA

CCGCTTCTGGGCGCTGATGGACGAGCCCGGCCCGCTGATCGAAGCGATCG

AATACTGA

Example 2: Expression of the Enzyme

The transaminase gene in Example 1 was linked to pET28a using an enzyme, and the restriction enzyme sites were Nde I & Hind III. The linked vector was transformed into host *Escherichia coli* BL21 competent cells. The constructed strains were seeded into TB medium, shaken at 200 rpm, at 30° C., and induced overnight with IPTG having a concentration of 0.1 mM. Then the strains were collected. Cells were resuspended in phosphate buffered (50 mM, pH 7.0), then were homogenized and disrupted. The expression effect was analyzed by SDS-PAGE.

Example 3 Synthesis of Compounds 6, 7, and 8

2,2-dimethyl-5-[2-(2,4,5-trifluorophenyl) acetyl]-[1,3] dioxane-4,6-dione (purchased from Jiangsu Baju Pharmaceutical Co., Ltd.) was suspended in 3 times toluene, and morpholine (1 eq) was slowly added under stirring. The reaction solution was stirred at room temperature for 1 h, and the temperature was raised to 110° C. under reflux for 16 h under nitrogen protection. TLC showed the reaction was complete and HPLC showed the starting material <1%. After cooling and concentrating, compound 6 was obtained.

After test: $^1$HNMR (400 MHz, DMSO-D6) δ7.52-7.45 (m, 1H), 7.40-7.33 (m, 1H), 3.91 (s, 2H), 3.76 (s, 2H), 3.53-3.51 (t, 4H), 3.44-3.42 (d, 2H), 3.41-3.32 (t, 2H).

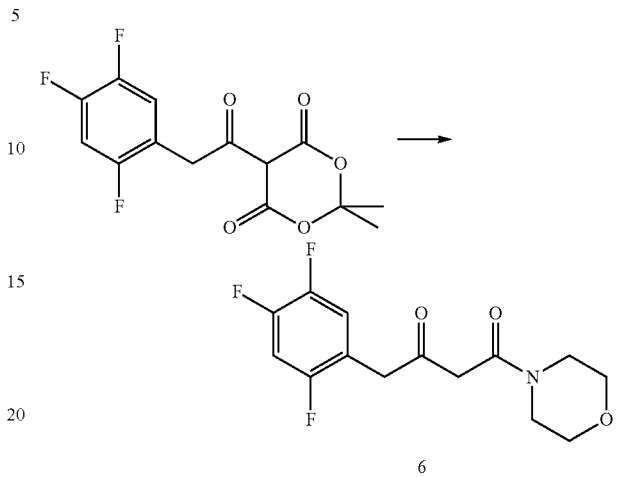

Using the same synthetic method, compounds 7 and 8 were synthesized by replacing morpholine with N-methylpiperazine or piperazine, respectively.

Example 4 Substrate Profiles of Transaminase Amino Donors

Reaction Formula:

1-(3-(trifluoromethyl)-5,6-dihydro-[1,2,4] triazolo [4,3-a] pyrazine-7 (8H)-yl)-4-(2,4,5-trifluorophenyl) butane-1,3-dione+amino donor→(3R)-3-amino-1-[3-(trifluoromethyl)-5,6-dihydro-1,2, 4-triazolo [4,3-a] pyrazine-7 (8H)-yl]-4-(2,4,5-trifluorophenyl) butan-1-one+carbonyl compound of an amino donor after deamination Reaction Conditions:

In 1 ml of 0.2M TEA-HCl buffer (pH 8.0), 0.1 ml of DMSO, 0.1 ml of 20 mM pyridoxal phosphate, 25 mg of 1-(3-(trifluoromethyl)-5,6-dihydro-[1,2,4] triazolo [4,3-a] pyrazine-7(8H)-yl)-4-(2,4,5-trifluorophenyl) butane-1,3-dione, 20 mg of amino donor, 0.5 ml of transaminase (with a protein concentration of 20 mg/mL) were added. After reacting at 45° C. for 6 hours, the reaction was terminated with acetonitrile. The conversion rates of the amino donors in the reaction systems were detected (see Table 2).

TABLE 2

| Conversion rates of different amino donors | |
|---|---|
| Amino donor | conversion rate |
| α-Phenethylamine | 31% |
| β-aminobutyric acid | 2% |
| Glycine | 0 |
| Alanine | 3.6% |
| Isopropylamine | 35% |

Example 5 Substrate Profiles of Transaminase Amino Receptors

Reaction Formula:

Isopropylamine+amino receptor→acetone+amino compound of an amino receptor after ammonification Reaction Conditions:

In 1 ml of 0.2M TEA-HCl buffer (pH 8.0), 0.1 ml of DMSO, 0.1 ml of 20 mM pyridoxal phosphate, 0.2 ml of 4M isopropylamine (pH 8.0), 20 mg of amino acceptor, 0.5 ml of transaminase (with a protein concentration of 20 mg/mL) were added. After reacting at 45° C. for 6 hours, the reaction was terminated with acetonitrile. The conversion rates of the amino receptors in the reactions were detected (see Table 3).

TABLE 3

Conversion rates of different amino receptors

| Amino receptor | Conversion rate | ee value | Product configuration |
|---|---|---|---|
| acetophenone | 5% | 98% | R |
| 1-(3-hydroxyphenyl)ethanone | 0 | | |
| 1-(m-tolyl)ethanone | 0 | | |
| ethyl acetoacetate | 2% | 98% | R |
| acetoacetic acid | 10% | 99% | R |
| 1-(3-(trifluoromethyl)-5,6-dihydro-[1,2,4]triazolo[4,3-a]pyrazin-7(8H)-yl)-4-(2,4,5-trifluorophenyl)butane-1,3-dione | 22% | 99% | R |
| 1-morpholino-4-(2,4,5-trifluorophenyl)butane-1,3-dione | 20% | 99% | R |
| 1-(4-methylpiperazin-1-yl)-4-(2,4,5-trifluorophenyl)butane-1,3-dione | 17% | 98% | R |

TABLE 3-continued

Conversion rates of different amino receptors

| Amino receptor | Conversion rate | ee value | Product configuration |
|---|---|---|---|
| ![structure] | 16% | 98% | R |

Example 6 Further Synthesis of Sitagliptin from Compound 6a

Compound 6a after test: $^1$HNMR (400 MHz, DMSO-D6) 67.46-7.38 (m, 2H), 3.53-3.49 (m, 4H), 3.40-3.37 (t, 4H), 3.24-3.21 (t, 1H), 2.66-2.52 (d, 1H), 2.54-2.52 (d, 1H), 2.31-2.30 (d, 2H), 1.56 (s, 2H).

Aqueous solution of lithium hydroxide (2-3 eq lithium hydroxide, 3 times of water) was prepared and compound 6a was added. After heating to 95° C., the reaction lasted for about 16 h. TLC showed that the basic reaction was completed. After cooling, dichloromethane was used for extraction and the raw materials were recovered. Slowly adjust the pH to 5.5-5.8 (<10° C.) with concentrated hydrochloric acid in the aqueous phase ice bath. Pale yellow solid of (R)-3-amino-4-(2,4,5-trifluorophenyl) butyric acid was obtained after filtration, washing and drying.

(R)-3-amino-4-(2,4,5-trifluorophenyl) butyric acid was dissolved in 20 times aqueous solution of sodium hydroxide (10 eq NaOH), and boc anhydride (Di-tert-butyl dicarbonate) was added dropwise (3 eq) at a controlled temperature of 25±3° C., and continued the adding dropwise (0.3 eq) at 25-30° C. to use up the raw materials. HPLC was used to track the raw materials until they were <0.5%. The impurities were extracted twice with 5 times dichloromethane, and the dichloromethane was mixed and washed twice with water. After mixing the aqueous phases, the pH was adjusted to 2.5-3.0 at 10-20° C. with 1N hydrochloric acid. After filtration, it was beaten with 50 times water. HPLC detection showed the single impurities were <0.1%. After vacuum drying at 20-25° C., the product Boc-(R)-3-amino-4-(2,4,5-trifluorophenyl) butyri acid was obtained.

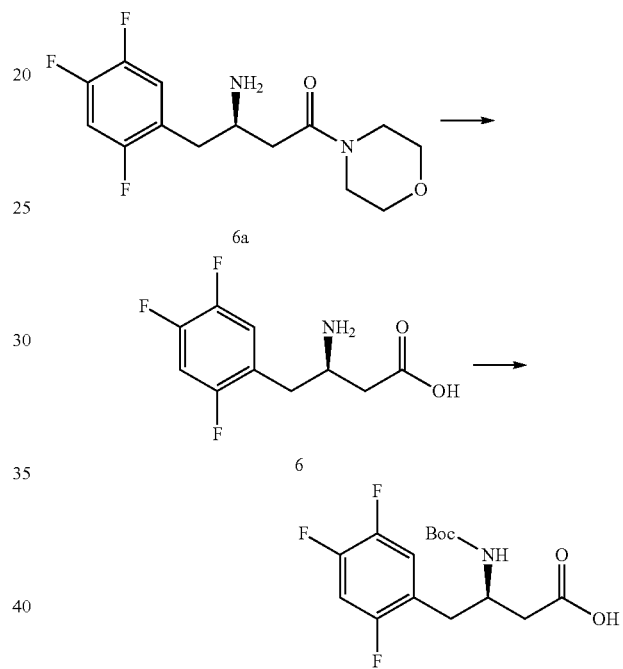

The above detailed description of the invention is intended to enable the skilled in the art to understand and implement the content of the invention, but not to limit the protection scope of the invention. Any equivalent change or modification according to the spiritual essence of the invention should be within the protection scope of the present invention.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A method for producing a chiral amine, comprising:
   (a) carrying out a reaction shown in equation I to form a chiral amine in a liquid reaction system, using a prochiral carbonyl compound as a substrate, reacting the substrate with an amino donor in the presence of a prosthetic group and under the catalysis of a stereoselective transaminase; and
   (b) isolating the chiral amine from the reaction system after carrying out the reaction in (a), wherein the stereoselective transaminase has an amino acid sequence having at least 90% sequence identity to the amino acid sequence shown in SEQ ID NO: 1; and
   wherein the prochiral carbonyl compound comprises any one of compounds 6-8, or a pharmaceutically acceptable salt thereof:

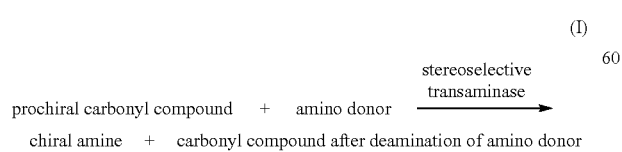

(I)

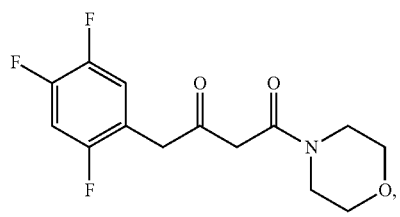

6

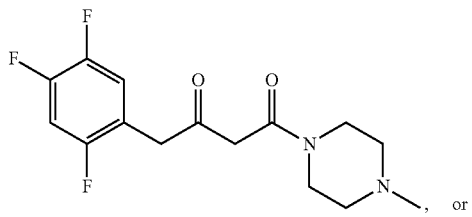

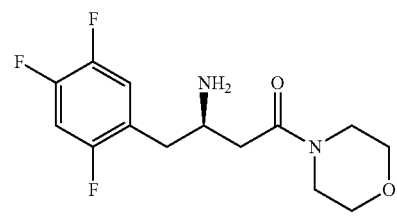

2. The method of claim 1, wherein the chiral amine is used as a precursor for producing sitagliptin and the precursor is selected from group consisting of compound 6a, compound 7a, and compound 8a.

3. The method of claim 1, wherein the chiral amine produced comprises any one of compounds 6a-8a or a pharmaceutically acceptable salt thereof:

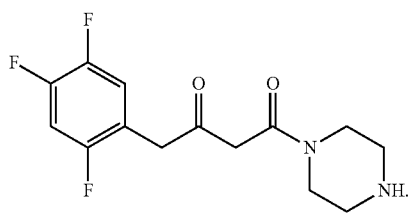

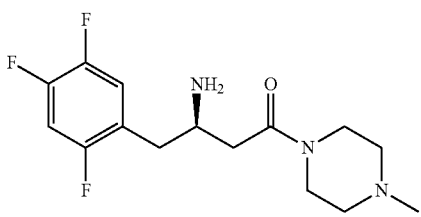

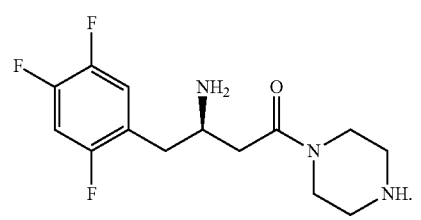

4. The method according to claim 1, wherein the amino donor comprises α-phenethylamine, β-aminobutyric acid, glycine, or isopropylamine.

5. The method according to claim 1, wherein the prochiral carbonyl compound is selected from the group consisting of compounds 6-8,

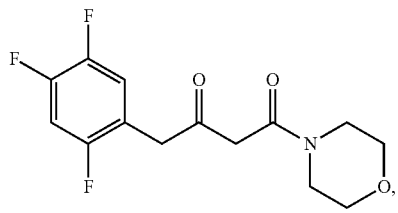

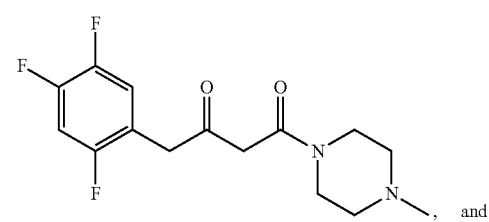

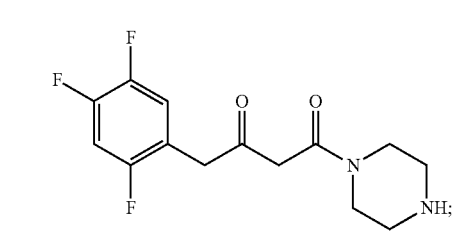

and wherein the chiral amine produced is used as a precursor for producing sitagliptin.

6. A method for producing a chiral amine, comprising the steps of:

1) culturing a chiral amine producing Escherichia bacterial strain comprising a modification to express an R-selective-ω-transaminase having an amino acid sequence having at least 90% sequence identity to the amino acid sequence shown in SEQ ID NO: 1 under production conditions sufficient to induce the expression of the (R)-selective-ω-transaminase;

2) homogenizing and disrupting the cultured chiral amine producing Escherichia bacterial strain;

3) adding the disrupted cultured chiral amine producing Escherichia bacterial strain to a liquid reaction system comprising a prochiral carbonyl compound and an amino donor;

4) carrying out the reaction in the liquid reaction system to obtain the chiral amine; and 5) isolating the chiral amine from the liquid reaction system of 4); and wherein the prochiral carbonyl compound comprises any one of compounds 6-8, or a pharmaceutically acceptable salt thereof:

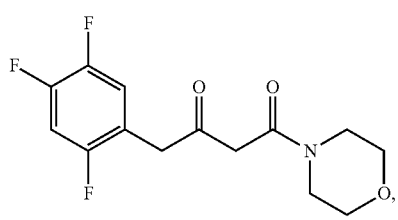

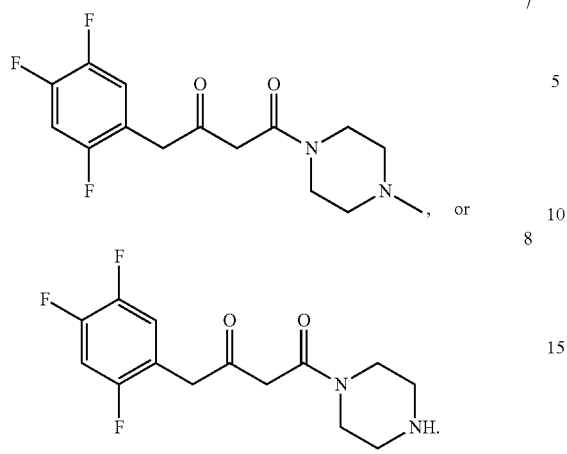

7. The method for producing a chiral amine according to claim 6, wherein the amino donor comprises α-phenethylamine, β-aminobutyric acid, glycine, or isopropylamine.

8. The method of claim 6, wherein the modification to express an R-selective-ω-transaminase is expression of a full-length transaminase gene selected from the group consisting of a nucleotide sequence having at least 90% sequence identity to the sequence shown in SEQ ID NO: 2 and a complementary sequence thereof.

* * * * *